(12) United States Patent
Yang et al.

(10) Patent No.: US 10,228,296 B2
(45) Date of Patent: Mar. 12, 2019

(54) METHOD OF OPERATING A TAYLOR-COUETTE DEVICE EQUIPPED WITH A WALL SHEAR STRESS SENSOR TO STUDY EMULSION STABILITY AND FLUID FLOW IN TURBULENCE

(71) Applicant: SCHLUMBERGER TECHNOLOGY CORPORATION, Sugar Land, TX (US)

(72) Inventors: Dingzheng Yang, Edmonton (CA); Dmitri Eskin, Melrose, MA (US); Shawn David Taylor, Reading, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 176 days.

(21) Appl. No.: 15/231,253

(22) Filed: Aug. 8, 2016

(65) Prior Publication Data
US 2018/0038780 A1    Feb. 8, 2018

(51) Int. Cl.
*G01N 11/10*    (2006.01)
*G01L 1/00*    (2006.01)
*G01N 11/14*    (2006.01)

(52) U.S. Cl.
CPC ............... *G01L 1/00* (2013.01); *G01N 11/14* (2013.01)

(58) Field of Classification Search
CPC ......... G01L 1/00; G01L 1/048; G01L 5/0047; G01N 11/04
USPC ........................................................ 73/54.23
See application file for complete search history.

(56) References Cited

U.S. PATENT DOCUMENTS

| 2,295,740 | A | 9/1942 | Keen |
| 3,456,494 | A | 7/1969 | Zimmer |
| 4,077,251 | A | 3/1978 | Winter |
| 4,174,907 | A | 11/1979 | Suh et al. |
| 5,209,108 | A | 5/1993 | Shackelford |

(Continued)

FOREIGN PATENT DOCUMENTS

WO    WO 2015069260 A1 *  5/2015    ............. G01N 11/04

OTHER PUBLICATIONS

Authors: Gregory S. Lewis and Harry L. Swinney, Title: Velocity structure functions, scaling, and transitions in high-Reynolds-number Couette-Taylor flow, Date: May 1999, Publisher: The American Physical Society, Physical Review E, vol. 59, No. 5, pp. 5457-5467.*

(Continued)

*Primary Examiner* — Lisa Caputo
*Assistant Examiner* — Roger Hernandez-Prewit

(57) ABSTRACT

Methods may include emplacing an emulsion into an annular region of a Taylor-Couette (TC) device; flowing the emulsion through the annular region created by a first annular surface and a second annular surface; contacting one or more shear sensors disposed on a surface of the annular region with the flowing emulsion, wherein contact with the one or more shear sensors generates a signal that scales with shear stress exerted by the flowing emulsion, and determining one or more of wall shear stress from the signal obtained from the one or more shear sensors. Methods may also include determining the apparent viscosity of the fluid composition from the stress measured on the wall of the TC device.

20 Claims, 5 Drawing Sheets

(56) References Cited

U.S. PATENT DOCUMENTS

| | | | |
|---|---|---|---|
| 5,306,734 | A | 4/1994 | Bass et al. |
| 5,370,824 | A | 12/1994 | Nagano et al. |
| 5,394,738 | A | 3/1995 | Bass et al. |
| 5,538,191 | A | 7/1996 | Holl |
| 5,959,194 | A | 9/1999 | Nenniger |
| 6,471,392 | B1 | 10/2002 | Holl et al. |
| 6,742,774 | B2 | 6/2004 | Holl |
| 6,752,529 | B2 | 6/2004 | Holl |
| 6,807,849 | B1 | 10/2004 | Reed et al. |
| 6,874,353 | B2 | 4/2005 | Johnson et al. |
| 6,959,588 | B2 | 11/2005 | Zougari et al. |
| 6,994,330 | B2 | 2/2006 | Holl |
| 7,150,183 | B2 | 12/2006 | Kharrat et al. |
| 7,581,436 | B2 * | 9/2009 | Eskin et al. .......... G01N 11/14 73/54.31 |
| 8,093,304 | B2 | 1/2012 | Varadaraj et al. |
| 8,276,463 | B2 | 10/2012 | Sheverev et al. |
| 2004/0255649 | A1* | 12/2004 | Zougari et al. ........ G01N 15/04 73/61.62 |

OTHER PUBLICATIONS

Authors: Nathanael J. Inkson, Jose Plasencia, Simon Lo, Title: Predicting emulsion Pressure Drop in Pipers Through CFD Multiphase Theology Models, Date: Jun. 17-19, 2014, Publisher: 10th International Conference on CFD in Oil & Gas, Matallurgical and Process Industries SINTEEF, Tronheim, Norway, pertinent pp. 1-6.*

Authors: Sander G. Huisman, Sven Scharnowski, Christian Cierpka, Christian J. Kahler, Detlef Lohse, and Chao Sun, Title: Logarithmic Boundary Layers in Strong Taylor-Couette Turbulence, Date: Jun. 26, 2013, Publisher: American Physical Society, PRL 110, 264501, pp. 264501-1 through 264501-5.*

Author: Russell J. Donnelly, Title: Evolution of Instrumentation for Taylor-Couette Flow, Date: 1992, Publisher: Plenum Press. New York, pp. 1-27.*

Author: Haoyu Wang, Title: Experimental and numerical study of Taylor-Couette flow, Date: 2015, Publisher: Iowa State University Digital Repository, Graduate Theses and Dissertations, pp. total: 173.*

Authors: Anthony Bacon, Sean Cook, Corwin Holmes and Jennifer Hoskins, Title: Re-Design of a Shear-Stress Sensor Load Cell for Liquid Flows, Date: Dec. 12, 2007, Publisher: University of Michigan, ME450, Fall 2007, Final Report, pp. 1-38.*

Authors: Dennis P.M. van Gils, Gert-Wim Bruggert, Daniel P. Lathrop, Chao Sun, and Detlef Lohse, Title: The Twente turbulent Taylor-Couette (T3C) facility: Strongly turbulent (multiphase) flow between two independently rotating cylinders, Date: Feb. 24, 2011, Publisher: Rev. Sci. Instrum. 82, 025105, pp. 1-14.*

Author: Van Boekel, Title: Influence of fat crystals in the oil phase on stability of oil-in-water emulsions, Date: 1980, Publisher: Center for Agricultural Publishing and Documentation, Wageningan, pp. 107.*

Authors: Nicolas Huang et al., Title: Viscosity of a dense suspension in Couette flow, Date: 2007, Publisher: Journal Fluid Mech., vol. 590, pp. 497-507.*

Angle, Chandra W., et al, "Size Distributions and Stability of Toluene Diluted Heavy Oil Emulsions", A.I.Ch.E. Journal, vol. 52, No. 3 (Mar. 2006) pp. 1257-1266.

Dodge, D.W., et al., "Turbulent Flow of Non-Newtonian Systems", A.I.Ch.E. Journal, vol. 5, No. 2 (Jun. 1959) pp. 189-204.

Hinze, J.O. et al., "Fundamentals of Hydrodynamic Mechanism of Splitting in Dispersion Processes," A.I.Ch.E. Journal, vol. 1, No. 3 (Sep. 1955) pp. 289-295.

Eskin, Dmitry, "An Engineering Model of a Developed Turbulent Flow in a Couette Device", Chemical Engineering and Processing vol. 49, (2010) pp. 219-224.

Fuller, Gerald G. et al, "Complex Fluid-Fluid Interfaces: Reology and Structure", Annu. Rev. Chem. Biomol. Eng. pp. 519-543.

Kokal, Sunil, "Crude Oil Emulsions: A State-Of-The-Art Review", Society of Petroleum Engineers, SPE 77497, Oct. 2002, 11 pages.

Lathrop, Daniel P. et al, "Turbulent Flow Between Concentric Rotating Cylinders at Large Reynolds Number," The American Physical Society, vol. 68, No. 10, Mar. 9, 1992, 5 pages.

Phan-Thien, N. et al, "Differential Multiphase Models for Polydispersed Suspensions and Particulate Solids", J. Non-Newtonian Fluid Mech., vol. 72 (1997) pp. 305-318.

Spiecker, P. M. et al, "Interfacial Rheology of Petroleum Asphaltenes at the Oil-Water Interface", American Chemical Society, (2004) pp. 4022-4032.

Van Gilst, Dennis P.M., et al., The Importance of Bubble Deformability for Strong Drag Reduction in Bubbly Turbulent Taylor-Couette Flow, J. Fluid Mech. (2013), vol. 722, 31 pages.

\* cited by examiner

METHOD OF OPERATING A TAYLOR-COUETTE DEVICE EQUIPPED WITH A WALL SHEAR STRESS SENSOR TO STUDY EMULSION STABILITY AND FLUID FLOW IN TURBULENCE

BACKGROUND

Emulsion stability and rheology are of interest in various applications including in the food, pharmaceutical, cosmetic, and petroleum industries. For example, in petroleum industry, water-in-oil emulsion formation may lead to dramatic increase in viscosity over that of oil or water alone, which can induce pressure losses and increase operation costs. While the presence of natural and/or added surfactants may stabilize emulsified fluid systems by reducing the coalescence of dispersed phase droplets under static conditions, emulsion stability and corresponding rheology may change under flow conditions encountered in various forms of piping used in the wellbore and during transport. Proper characterization of emulsion stability is then important to ensure various physical or chemical properties of an emulsion, such as the tendency of droplets of the internal phase to coalesce, remain favorable under flow conditions for a given application.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, methods in accordance with the present disclosure may include emplacing an emulsion into an annular region of a Taylor-Couette (TC) device, wherein the annular region is defined by a first annular surface and a second annular surface that are concentric with respect to one another about a common center, wherein the first annular surface is offset from the center by a first radius R and the second annular surface is offset from the center by a second radius $r_0$, wherein R is greater than $r_0$; flowing the emulsion through the annular region created by the first annular surface and the second annular surface; contacting one or more shear sensors disposed on a surface of the annular region with the flowing emulsion, wherein contact with the one or more shear sensors generates a signal that scales with shear stress exerted by the flowing emulsion; and determining one or more of wall shear stress from the signal obtained from the one or more shear sensors.

In another aspect, methods in accordance with the present disclosure may include emplacing an emulsion into an annular region of a Taylor-Couette (TC) device, wherein the annular region is defined by a first annular surface and a second annular surface that are concentric with respect to one another about a common center, wherein the first annular surface is offset from the center by a first radius R and the second annular surface is offset from the center by a second radius $r_0$, wherein R is greater than $r_0$; flowing the fluid composition in a chamber created by the first annular surface and the second annular surface; measuring the stress exerted on a wall of the TC device; and determining the apparent viscosity of the fluid composition from the stress measured on the wall of the TC device.

Other aspects and advantages of the invention will be apparent from the following description and the appended claims.

DETAILED DESCRIPTION

Figure 1:
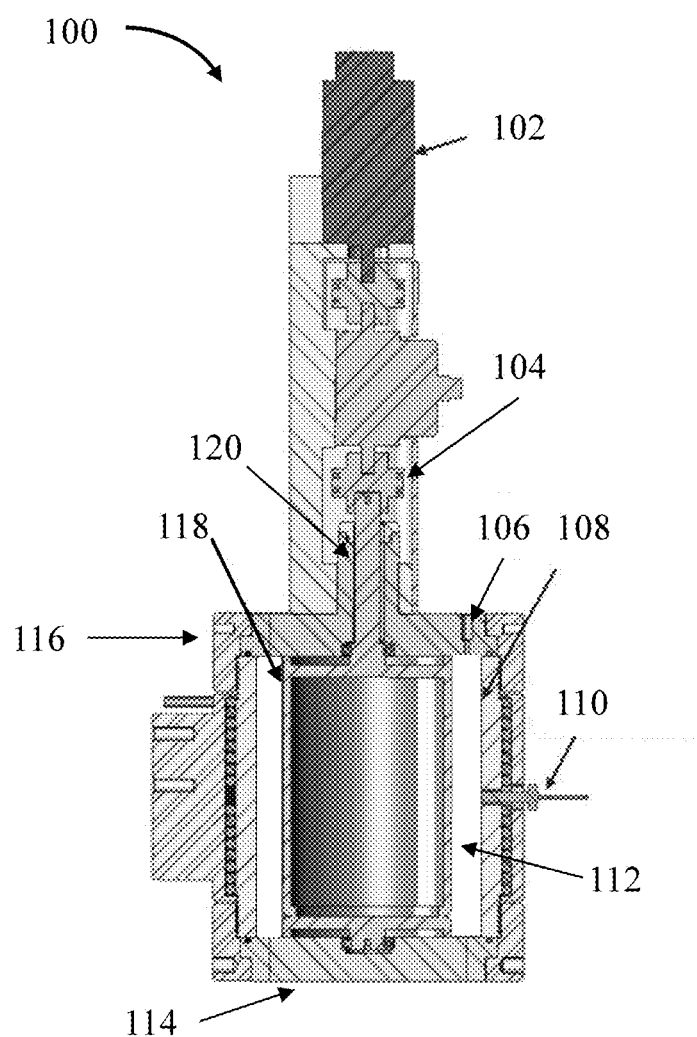
FIG. 1 is an illustration depicting an embodiment of a Taylor-Couette device in accordance with the present disclosure.

Embodiments disclosed herein are directed to methods and devices for characterizing viscosity and stability of emulsions generated under turbulent flow conditions. Methods and devices in accordance with the present disclosure may provide information on emulsion stability under flow conditions that mimic those encountered during pipeline transport. In one or more embodiments, methods may incorporate one or more Taylor-Couette fluid flow models to calculate the wall shear, which may be used in conjunction with wall shear stress measured using a suitable sensor to determine one or more of the Reynolds number, viscosity, and emulsion stability for a given fluid composition.

In one or more embodiments, fluid properties of emulsions under dynamic conditions may be quantified using a Taylor-Couette (TC) device. An emulsion is a mixture in which one phase is dispersed into another. It follows from the second law of thermodynamics that, in absence of any stabilization methods, emulsions tend to minimize interface surface such as by flocculation or coalescence of droplets. Under flow conditions, the addition of surfactants may reduce interfacial tension, making an emulsion kinetically stable. Surfactants may adsorb at the liquid-liquid interface, forming either a monolayer or a three dimensional network. Three dimensional surfactant networks created at a liquid-liquid interface may stabilize emulsions to a greater degree and enhance rheological behavior such as viscosity in a given mixture when compared to surfactant monolayers.

In some cases, surfactant films present at the interface of internal and external emulsion phases may change over time from a surfactant monolayer to a three dimensional network, which can increase the film elastic modulus. For example, in crude oil, natural surfactants such as those present in the asphaltene fractions may gravitate naturally to the oil/water interface and increase the density of the surfactant film. Interfacial films in stable emulsions may exhibit elastic properties characterized by increased resistance to shear and extensional deformation.

For most applications, an emulsion is considered stable under known flow conditions when its properties such as the coalescence rate of the internal phase are relatively low and do not change with time. However, emulsions and other complex fluid compositions may undergo structural changes under turbulent flow conditions, which may induce coalescence of internal phase droplets that are otherwise regarded as stable under static conditions. Mobile liquid/liquid interface causes coalescing internal phase droplets. Such a dispersed system is characterized by a lower viscosity than a stable emulsion characterized by rigid interfaces. Rigid droplet interface prevents coalescence.

TC devices in accordance with the present disclosure are composed of two co-axial cylinders, one or both of which are able to rotate, and may reproduce pipe flow conditions on a laboratory scale. In one or more embodiments, wall shear sensors in accordance with the present disclosure may include sensors mounted within the fluid chamber created between concentric cylinders. In some embodiments, TC devices may be designed to utilize a small liquid volume for testing viscosity and emulsion stability, while maintaining the ability to create flow patterns and corresponding turbulence structures similar to those experienced in pipe flow.

Methods in accordance with the present disclosure may use wall shear stress as one parameter that describes flow in the vicinity of the solid surface boundary of the outer cylinder of the TC device. For example, direct measurement of the wall shear stress generated by a fluid flow under turbulent conditions may be determined by quantifying the tangential force exerted directly on the surfaces within the TC device. In some embodiments, time-averaged and time-resolved wall shear stress may be used to characterize the average properties of an emulsion, such as fluid viscosity and drag reduction effects.

Results obtained from wall shear stress measurements within a TC device in accordance with the present disclosure may also validate various engineering models describing the behavior of emulsions in turbulent flow conditions. As an example, the model presented in Eskin, D. (2010) "An engineering model of a developed turbulent flow in a Couette device", *Chem. Eng. & Process.* 49, 219-224 (the Eskin model) establishes the relationship between the rotation speed and the torque applied to the rotor.

The Eskin model describes the forces on the fluids within the TC device in terms of non-dimensional torque G and Reynolds number Re in a way that is not limited to a certain radius ratio. In Eq. 1, a model for Couette flow in a TC device is provided in terms of Re and G, where $\eta$ is the radius ratio $r_0/R$, $\alpha$ and $\beta$ are non-dimensional functions of the radius ratio $\eta$, G is the non-dimensional torque, and $\xi_2$ is an empirical constant.

$$\alpha(\eta)\frac{Re}{\sqrt{G}} = \ln\sqrt{G} + \beta(\eta) + \xi_2 \quad (1)$$

The non-dimensional functions $\alpha$ and $\beta$ are defined by Eqs. 2 and 3, where $\kappa$ is the von Karman constant.

$$\alpha = \frac{\kappa}{1/\eta + \eta} \frac{\sqrt{2\pi}}{1-\eta} \quad (2)$$

$$\beta = \frac{2}{1/\eta + \eta} - \ln\left(\frac{1+\eta}{1-\eta}\right) \quad (3)$$

Empirical constant $\xi_2$ is given by Eq. 4, where $\xi_1$ is an empirical constant, b is the dimensionless thickness of the boundary sub-layer and buffer layer within a TC device. In one or more embodiments, $\xi_2$ may be set equal to 0.406 in accordance with the Eskin model.

$$\xi_2 = \kappa \xi_1 - \ln\sqrt{2\pi} = \kappa[\lambda - (1 + \ln b)/\kappa] - \ln\sqrt{2\pi} \quad (4)$$

From Eqs. 1-4, if torque is known for a given TC device, the shear stress on the inner cylinder surface may be determined and used to calculate the shear stress on the outer cylinder surface. Thus, the rotation speed of the inner cylinder may be used to calculate the shear stress on the outer cylinder using the model.

To determine relative viscosity of an emulsion in the TC device, the viscosity is allowed to vary in the model until the calculated wall shear stress coincides with that measured by the wall shear stress sensor. The apparent viscosity (or emulsion viscosity) measured is then converted to the relative viscosity, as discussed with respect to FIG. 5 below, by dividing the apparent viscosity by the viscosity of the continuous phase alone.

Emulsion characterization in accordance with the present disclosure may involve the use of a TC device equipped with a wall shear stress sensor. With particular respect to FIG. 1, an embodiment of a TC device 100 is shown containing a central chamber created from co-axial cylinders. TC device 100 includes a top wall 116, outer cylinder 108, inner cylinder 118, and bottom wall 114 that define the boundaries of an annulus 112. During operation, fluids may be loaded into the annulus 112 through one or more fluid paths such as fluid path 106. The inner cylinder 118 is mounted on bearings and rotates independently of the outer cylinder 108. Shaft 120 is connected to and extends from inner cylinder 118. Motor 102 is mechanically coupled to shaft 120 by means of a coupling device 104, which may be a magnetic coupler, a rigid coupler, a flexible coupler, or other suitable coupling mechanism. In some embodiments, the motor 102 is configured to operate over a wide range of rotational speeds (e.g., 100-20,000 rpm) and rotate inner cylinder 118 at different angular velocities.

In one or more embodiments, TC devices in accordance with the present disclosure may be modified to contain one or more shear stress sensors 110 configured to contact fluids placed within annulus 112. The wall shear stress sensor 110, installed on the inner wall of outer cylinder of TC device, measures shear stress exerted by fluid flow within the annulus 112. In some embodiments, variations of the shear stress may provide information regarding various fluid properties including, for example, changes of emulsion rheology and stability under flow conditions.

Other instrumentation can be added to embodiments of the TC device 100 as application demands. For example, devices may include components for pumping fluids into annulus 112 or maintaining pressure within the system. In addition, heating and/or cooling elements may be included within the TC device to control the temperature of fluids. In some embodiments, one or more temperature sensors and one or more pressure sensors may be mounted adjacent the annulus 112 to measure fluid temperature and pressure therein. In particular embodiments, the rotational speed of the inner cylinder 118 may be measured through the use of a proximity sensor that measures the rotational speed of the shaft 120 mechanically coupled to the inner cylinder 118.

The fluid flow in the annulus 112 of the TC device 100 can be studied in terms of the dimensionless torque G and the Reynolds number $Re_c$ for such fluid flow. The dimensionless torque G is defined as a function of the torque T related to the shear stress $\tau_w$ measured at the inner wall surface 104A of the outer cylinder 104 of the TC device 100 as follows:

$$G = \frac{T}{\rho v^2 L} \quad (5)$$

where torque $T=\tau_w 2\pi R^2 L$, $\tau_w$ is shear stress, R is the radius of the inner wall of the outer cylinder of the TC device, $\rho$ is the density of the fluid, $\nu$ is the kinematic viscosity of the fluid, and L is the height of the TC device annulus. For TC devices in accordance with the present disclosure, control of rotation of the inner cylinder (control of angular velocity) will also control torque, which may be combined with the rotation speed value in some embodiments to calculate the viscosity of the surrounding fluid.

In one or more embodiments, the Reynolds number $Re_c$ (or Re) for fluid flow in the annulus 112 of the TC device may be calculated as:

$$Re_c = \frac{\omega r_0 (R - r_0)}{\nu} \qquad (6)$$

where $r_0$ is the outer radius of the inner cylinder 118 of the TC device 100, R is the radius of the inner wall of the outer cylinder of the TC device, $\nu$ is the kinematic viscosity of the fluid, and w is the angular velocity of the inner cylinder 118.

Figure 2:
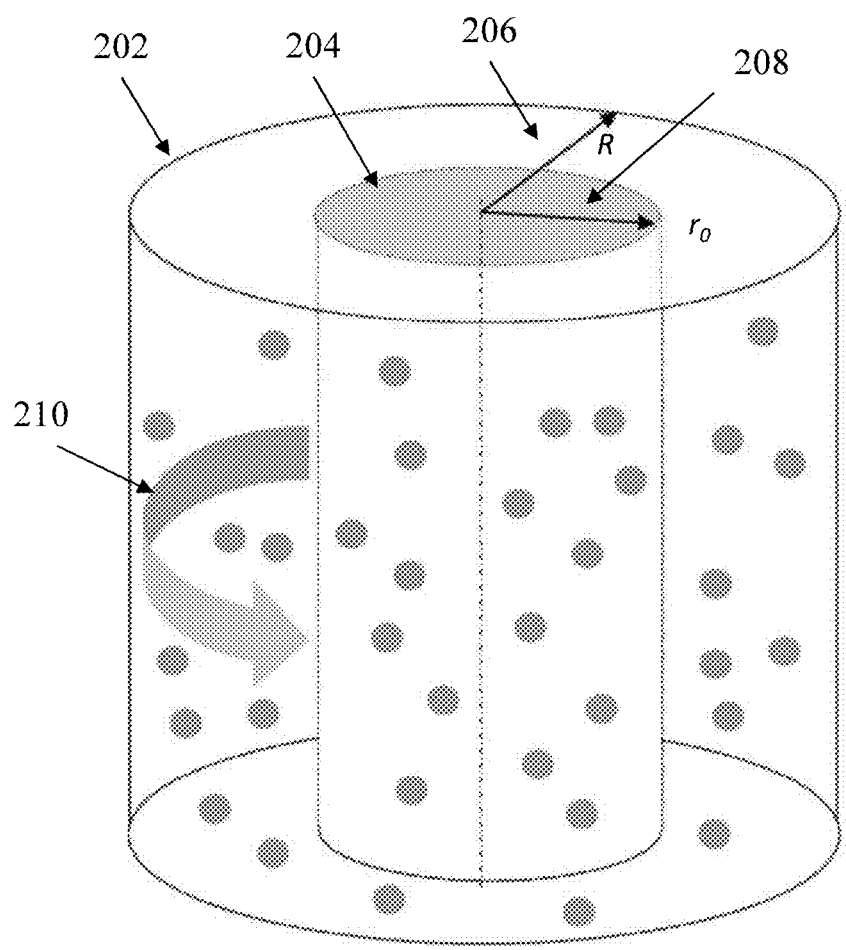
FIG. 2 is an illustration depicting a schematic diagram of an embodiment of a Taylor-Couette device in accordance with the present disclosure.

Another schematic of a TC device is shown in FIG. 2, with the radius R denoting the radius of the inner wall surface of the outer cylinder 202 and the radius $r_0$ denoting the radius of the outer surface of the inner cylinder 204. The annulus or gap 210 between the inner and outer cylinders has a width W of $(R-r_0)$ and a height of L. A fluid of a certain composition is loaded into the annulus 210, and the rotation of the inner cylinder at a given angular velocity is sufficient to initiate flow of the fluid in the annulus. In one or more embodiments, TC devices in accordance with the present disclosure may operate in the flow regime of $13{,}000 \leq Re_c \leq 10$. However, in some embodiments, the TC device may be operated at a Reynolds number $Re_c$ exceeding 13,000.

Figure 3:
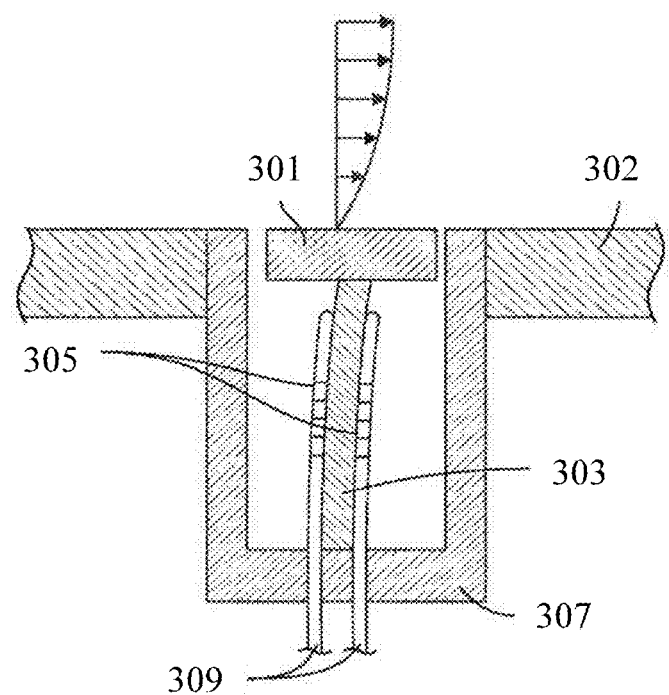
FIG. 3 is an illustration depicting an embodiment of a wall shear stress sensor in accordance with the present disclosure.

With particular respect to FIG. 3, the shear stress of the fluid at the inner surface of the wall of the outer cylinder 302 (corresponding to surface of the outside wall 108 of the TC device in FIG. 1) is measured using a wall shear stress sensor that combines a floating element 301 and a mechanical cantilever beam 303 with a micro-optical strain gauge (fiber Bragg grating or FBG) 305. Floating element 301 is in fluid contact and attached to the cantilever beam 303. The floating element is installed flush with the inner wall surface of the outer cylinder 302 in a sensor enclosure 307. Displacement of the floating element 301 leads to bending of cantilever beam 303. When the cantilever beam bends, the FBG is strained in a manner that shifts its optical spectrum. By interrogating the FBG with a light source via optical fibers 309, this strain (and therefore the shear stress) is measured by tracking the shift in the resonant wavelength. The shear stress is calculated as $\tau_w = k \Delta \lambda$, where k is the calibration coefficient and $\Delta \lambda$, is the shift in the resonant wavelengths.

In some embodiments, wall shear stress measuring sensors may be direct measurement force sensors employing a floating element that is brought in contact with the flow and a mechanical cantilever system which bends in response to shear stress applied to the sensor's surface. This bending is detected by two optical strain gauges called Fiber Bragg Gratings (FBGs), attached to either side of the cantilever beam. Bending causes strain in the FBGs which induces proportional shifts in their optical resonance frequencies. Wall shear sensors may include commercially available sensors such as REALSHEAR™ sensors available from Lenterra (Newark, N.J.).

TC devices in accordance with the present disclosure have a co-axial cylindrical geometry, where the inner cylinder rotates whereas the outer one is immobile. Emulsion characterization is initiated by charging two immiscible fluids into the TC device and generating an emulsion by operating the device in a turbulent regime. The wall shear stress sensor, installed on the outer cylinder TC device wall, provides accurate values of the shear stress exerted by a fluid flow. Moreover, the behavior of the emulsion in the TC may provide a reasonable estimation of emulsion behavior during pipeline transport, because the flow pattern in a TC device is reasonably similar to that in a pipe flow. During turbulent flow the dispersed phase of an emulsion is assumed to be uniformly distributed throughout the continuous phase.

In some embodiments, emulsion viscosity may be identified from the measured shear stress data by using known flow models such as the Eskin model for turbulent TC flow conditions. The Eskin model of a developed turbulent flow in a TC device is based in part on the well-known Prandtl Mixing Length theory, and is relatively simple and accurate for TC flow regimes in which the Reynolds Number exceeds 13,000. The validity of such methods of viscosity identification has been confirmed by comparison of viscosities, identified from experimental data obtained in the laboratory TC device, with those calculated by empirical correlation of the emulsion viscosity as a function of the dispersed phase volume fraction. For example, other models that may be used to describe the viscosity of an emulsified fluid in a TC device include those presented in Phan-Thien, N; Pham, D C. (1997) Differential multiphase models for polydispersed suspensions and particulate solids. *J. Non-Newtonian Fluid Mech.* 72, 305-318; and Krieger, I M; Dougherty, T J. (1959) A mechanism for non-Newtonian flow in suspensions of rigid spheres. *Trans. Soc. Rheol.* 3, 137-152.

The Phan-Thien-Pham model relates the relative emulsion viscosity $\eta_r$, representing a ratio of the emulsion viscosity $\mu_e$ to the viscosity of a continuous phase $\mu_c$, and the volume fraction of the dispersed phase $\phi$ according to the relationship shown in Eq. 7, where $K=\mu_d/\mu_c$, and $\mu_d$ is the dispersed phase viscosity.

$$\eta_r^{2/5} \left( \frac{2\eta_r + 5K}{2 + 5K} \right)^{3/5} = \frac{1}{1-\phi} \qquad (7)$$

The Krieger-Dougherty model relates the relative viscosity of a suspension, represented here as a stable emulsion, and the dispersed phase volume fraction. According to the model, the relative viscosity of a suspension of spherical solids particles can be evaluated according to Eq. 8, where $\phi_m$ is the disperse phase packing volume concentration. In some embodiments, methods in accordance with the present disclosure may select $\phi_m$ to be equal to 0.7 for the computational purposes.

$$\eta_r = \left(1 - \frac{\phi}{\phi_m}\right)^{-2} \qquad (8)$$

In some embodiments, apparent viscosity of an emulsion may be used to determine the overall emulsion stability. An emulsion that is unstable may have a mobile interface between the phases that decreases the measured viscosity, while more stable emulsions containing dispersed phase droplets with a relatively rigid interface may exhibit greater viscosity. The presence of additives such as surfactants may strengthen the interface between the fluid phases, which may in turn promote emulsion stability. Thus, identification of the emulsion viscosity from the shear stress data measured in a TC device may be used as a measure of whether an emulsion generated is stable or unstable in some embodiments.

In order to measure the stability of an emulsion under dynamic conditions, two immiscible fluids are charged into the TC device and an emulsion is generated by operating the device in a turbulent regime. In one or more embodiments, the viscosity of the emulsion may be calculated from the shear stress data measured by the wall shear stress sensor in combination with other variables such as the rotational speed of the TC device, the density, the viscosity of the continuous phase of the emulsion, and the volume fraction of a dispersed or internal phase. In some embodiments, emulsion viscosity may be determined from an empirical correlation as a function of the dispersed phase volume fraction. In addition, emulsion properties may also be monitored in real time for response to surfactants and other additives.

EXAMPLES

The present disclosure is further exemplified by the examples below which are presented to illustrate certain specific embodiments of the disclosure but are not intended to be construed so as to be restrictive of the spirit and scope thereof.

In a first example, a 50% emulsion of water in mineral oil and a mineral oil control is studied under turbulent conditions in a TC device equipped with a wall shear sensor in accordance with the present disclosure. Based on the rotational speed of the internal cylinder of the TC device, the Reynolds number of the fluid flow within the device may be calculated, while the wall shear sensor is used to determine the wall shear stress as a function of the Reynolds number.

Figure 4:
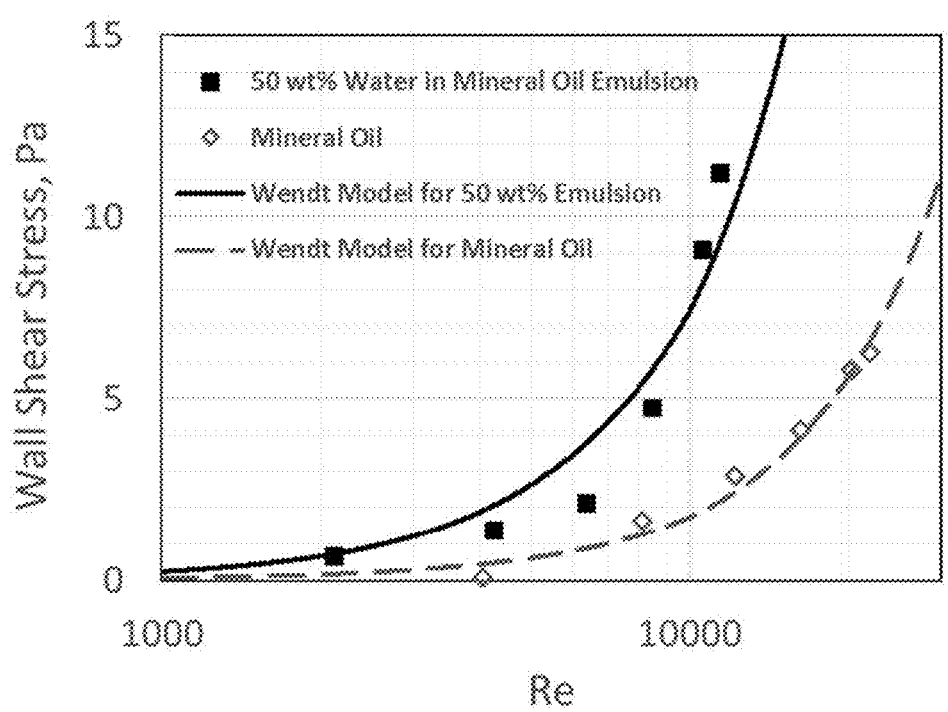
FIG. 4 is a graphical representation of wall shear stress as a function of Reynolds number for various samples analyzed in a Taylor-Couette device in accordance with the present disclosure.

With particular respect to FIG. 4, a plot of wall shear stress vs. the Reynolds number for flows investigated in a TC device. The dashed line shows the data computed for a pure mineral oil flow. The solid curve denotes the results of computations for a 50% dispersed phase by volume of water in mineral oil emulsion. Both curves were obtained from correlating the torque applied to the TC device inner cylinder and its rotation speed. The emulsion viscosity was identified by fitting the empirical Wendt model to the experimental data first described in F. Wendt, Turbulente Stromungen zwischen zwei rotierenden konaxialen Zylindern, Ing. Arch., 4, 577-595, 1933.

Data points in FIG. 4 indicate the shear stress exerted by a fluid flow in a TC device measured in accordance with the present disclosure, which shows good agreement between the calculated results that assume a constant viscosity and the measured data. This result shows that, a dense emulsion flowing in a turbulent TC flow may be regarded as a continuous fluid, and models for an equivalent fluid may be employed to describe dispersed turbulent emulsion TC flows. Thus, no significant dispersed phase stratification occurs across the TC device gap. It is also noted that the agreement of the data with the Wendt model is suitable for TC fluid flow below 13,000 Re, while turbulent fluid flows above 13,000 Re correlate to the Eskin model with smaller error.

Emulsion stability under flow conditions is determined in part by factors such as the ability of internal phase droplets to coalesce that is governed by the interfacial rigidity between the continuous and dispersed phases. The addition of certain surfactants may influence interfacial rigidity. For example, as surfactant increases, the rigid interface prevents dispersed phase droplet coalescence, maintaining a stable emulsion. Moreover, the apparent viscosity of the emulsion increases as a result of the enhanced friction between droplets possessing the rigid interface and the continuous fluid in a shear flow. At the limit, the viscosity of a stable emulsion reaches the viscosity of a suspension of solids, where the interface, by definition, is completely rigid. In one or more embodiments, a TC device, equipped with the shear stress sensor, may be used to study the evolution of the emulsion viscosity with time and under varying flow regimes. In some embodiments, the viscosity of an emulsion may be calculated using the Eskin model for fluid flow in a TC device.

In the next example, the effect of a surfactant was studied on samples of a water in mineral oil emulsion having varying volume fractions of internal water phase. During the experiment, the TC device was operated at a constant rotational speed, for different dispersed phase volume fractions and surfactant concentrations. With particular respect to FIG. 5, the relative viscosity of water in mineral oil emulsions is shown as a function of the dispersed phase volume fraction. The relative viscosity is defined as the ratio of the emulsion viscosity to the viscosity of the continuous phase in the absence of the internal phase.

The viscosity data points computed based on the TC device stress measurements for each volume fraction were then compared to existing models for stable and unstable emulsion viscosities in order to quantify the stability of the particular emulsion and volume fractions with or without surfactant. For example, if viscosity as a function of dispersed phase volume fraction approximated that for an emulsion characterized by mobile interface, then it may be concluded that the formed emulsion is unstable and coalescence of droplets is not suppressed under the given conditions. Intermediate states may also exist in which the dispersion viscosity is indicative of reduced interface mobility and that droplet coalescence is partially suppressed. In one or more embodiments, the emulsion viscosity may also be determined using the Eskin model of a single phase TC flow, particularly when the TC device is operated in turbulent flow regimes in excess of 13,000 Re.

Figure 5:
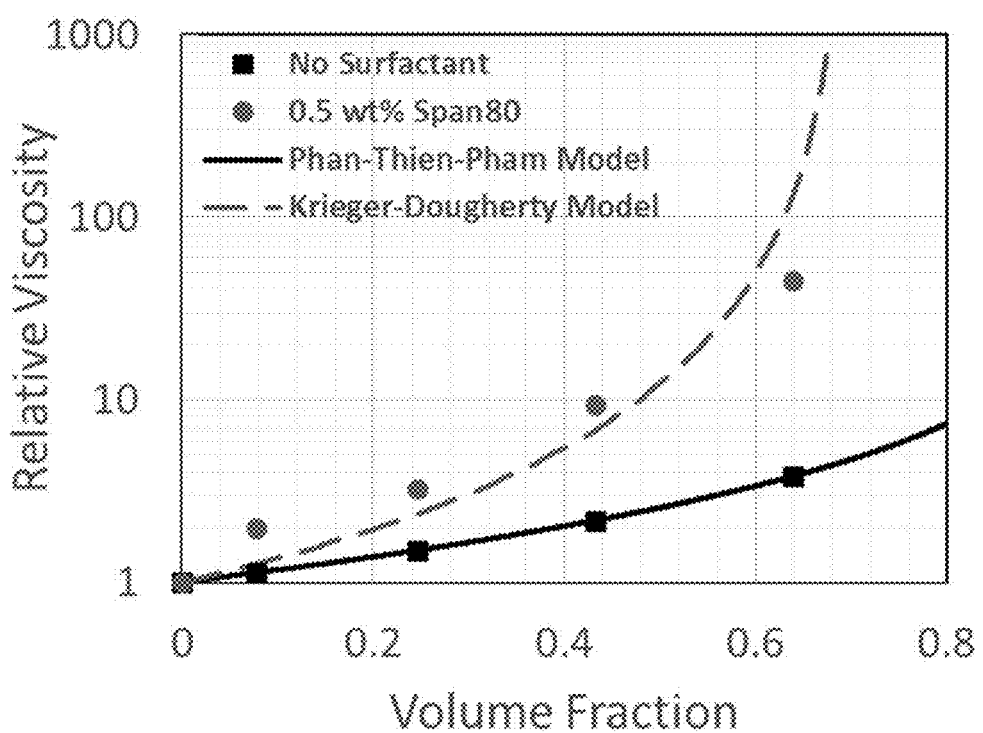
FIG. 5 is a graphical representation of relative viscosity as a function of volume fraction of an internal phase for various samples analyzed in a Taylor-Couette device in accordance with the present disclosure.

The curves in FIG. 5 were obtained by using the empirical correlations of emulsion viscosity as a function of dispersed phase volume fraction. The solid curve corresponds to the unstable emulsion without surfactant. Particularly, it is noted that the unstable emulsion increases in viscosity to a lesser degree than stable emulsions as the volume fraction of the dispersed phase increases. Models used to describe unstable emulsions containing a mobile fluid interface may include models such as the Phan-Thien-Pham Model, as used in the present example and described in Phan-Thien, N; Pham, DC., (1997) "Differential multiphase models for polydispersed suspensions and particulate solids", *J. Non-Newtonian Fluid Mech.* 72, 305-318.

The dashed line in FIG. 5 is calculated from the correlation for a stable emulsion. The overlaid data points denote shear stress measurements in a TC device in accordance with the present disclosure. Here, emulsion stability is indicated by an increase in viscosity with increasing internal phase volume fraction, which may be described by a number of models such as the Kreiger-Dougherty model described in Krieger, I M; Dougherty, T J., (1959) A mechanism for non-Newtonian flow in suspensions of rigid spheres. *Trans. Soc. Rheol.* 3, 137-152. Similarly, the emulsion may be regarded as stable if the calculated viscosity corresponds to the viscosity of suspension of solid particles, which may indicate that the liquid/liquid interface is rigid and coalescence is suppressed. As evidenced by FIG. 5, calculated and identified viscosities correlate well and the stable emulsion has much higher viscosity than the unstable one.

The TC device examples show that the emulsion viscosity as a function of the volume fraction of dispersed phase obeys the known correlations for two-phase systems. Further, it is noted that the viscosity of an unstable emulsion may be described by the Phan-Thein-Pham model that assumes a mobile interface, and the viscosity of a stable emulsion may be calculated using similar equations describing a suspension of solids characterized by immobile interface such as the Krieger-Dougherty model.

In one or more embodiments, wall shear stress may be monitored in real time using a TC device in accordance with the present disclosure equipped with a shear stress sensor for different stirring durations to characterize changes in emulsion stability or degradation of a surfactant under certain conditions over time such as temperature, pH, Reynolds number, and the like. In some embodiments, changes in viscosity of a monitored emulsion may be used to determine the degree of interface rigidity as a measure of emulsion stability.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method, comprising:
    emplacing an emulsion into an annular region of a Taylor-Couette (TC) device, wherein the annular region is defined by a first annular surface and a second annular surface that are concentric with respect to one another about a common center, wherein the first annular surface is offset from the center by a first radius R and the second annular surface is offset from the center by a second radius $r_0$, wherein R is greater than $r_0$;
    flowing the emulsion through the annular region created by the first annular surface and the second annular surface;
    contacting one or more shear sensors disposed on a surface of the annular region with the flowing emulsion, wherein contact with the one or more shear sensors generates a signal that scales with shear stress exerted by the flowing emulsion;
    determining one or more of wall shear stress from the signal obtained from the one or more shear sensors; and
    determining, based on the one or more of wall shear stress, whether dispersed phase droplets of the emulsion comprise a mobile interface having a first coalescence rate or an immobile interface having a second coalescence rate less than the first coalescence rate.

2. The method of claim 1, wherein the ratio of $r_0$ to R is in the range of 0.3 to 0.9.

3. The method of claim 1, wherein determining one or more of wall shear stress from the signal obtained from the one or more shear sensors comprises:
    determining the shear stress exerted on the wall of the TC device;
    fitting the measured shear stress exerted on a wall of the TC device to a model describing wall shear stress as a function of Reynolds number for the TC device; and
    determining a viscosity for the fluid composition.

4. The method of claim 3, wherein the emulsion is flowed through the annular region in a flow regime below 13,000 Re.

5. The method of claim 4, wherein the viscosity is determined by fitting wall shear stress as a function of Reynolds number according to a Wendt model.

6. The method of claim 3, wherein the emulsion is flowed through the annular region in a flow regime above 13,000 Re.

7. The method of claim 6, wherein the viscosity is determined by fitting wall shear stress as a function of Reynolds number according to a Eskin model.

8. The method of claim 1, said determining whether dispersed phase droplets of the emulsion comprise a mobile interface or an immobile interface comprising:
    determining, based on the one or more of wall shear stress, relative viscosity of the emulsion as a function of volume fraction of dispersed phase of the emulsion;
    comparing the relative viscosity of the emulsion as the function of volume fraction to a first expected relationship to determine whether a first match exists; and
    if the first match exists, determining that the dispersed phase droplets of the emulsion comprise the mobile interface and that the emulsion is unstable.

9. The method of claim 8, wherein said determining whether dispersed phase droplets of the emulsion comprise a mobile interface or an immobile interface further comprises:
    comparing the relative viscosity of the emulsion as the function of volume fraction to a second expected relationship to determine whether a second match exists; and
    if the second match exists, determining that the dispersed phase droplets of the emulsion comprise the immobile interface and that the emulsion is stable.

10. The method of claim 9, wherein a stable emulsion is defined by a Kreiger-Dougherty model.

11. The method of claim 9, wherein an unstable emulsion is defined by a Phan-Thien-Pham model.

12. The method of claim 1, wherein the one or more shear sensors are floating element-type strain sensors.

13. The method of claim 1, wherein the one or more shear sensors comprise one or more fiber Bragg gratings.

14. The method of claim 1, wherein the TC device is equipped to control one or more of temperature and pressure.

15. A method, comprising:
    emplacing an emulsion into an annular region of a Taylor-Couette (TC) device, wherein the annular region is defined by a first annular surface and a second annular surface that are concentric with respect to one another about a common center, wherein the first annular surface is offset from the center by a first radius R and the second annular surface is offset from the center by a second radius $r_0$, wherein R is greater than $r_0$;
    flowing the fluid composition in a chamber created by the first annular surface and the second annular surface;
    measuring the stress exerted on a wall of the TC device;
    determining the apparent viscosity of the fluid composition from the stress measured on the wall of the TC device; and determining, based on the apparent viscosity of the fluid composition, whether dispersed phase droplets of the emulsion comprise a mobile interface having a first coalescence rate or an immobile interface having a second coalescence rate less than the first coalescence rate.

16. The method of claim 15, wherein determining the apparent viscosity of the fluid composition comprises measuring the stress exerted on the wall of the TC device at multiple Reynolds values and fitting the measured values to a mathematical model.

17. The method of claim 16, wherein the mathematical model is a Wendt model.

18. The method of claim 15, wherein determining the apparent viscosity of the fluid composition comprises measuring the stress exerted on the wall of the TC device at one or more Reynolds values above 13,000 and fitting the measured values to a Eskin model.

19. The method of claim 15, wherein the device includes one or more shear sensors and a data acquisition system to receive data from said shear sensors.

20. The method of claim 15, wherein the sensor is a floating element-type strain sensor.

* * * * *